(12) United States Patent
Dietz et al.

(10) Patent No.: US 8,500,648 B2
(45) Date of Patent: Aug. 6, 2013

(54) REAL TIME ULTRASOUND CATHETER PROBE

(75) Inventors: Dennis R. Dietz, Littleton, CO (US);
Clyde G. Oakley, Centennial, CO (US);
Ryan C. Patterson, North Salt Lake City, UT (US); Johannes Haftmann, Heideck (DE)

(73) Assignee: W. L. Gore & Associates, Inc, Newark, DE (US)

( * ) Notice: Subject to any disclaimer, the term of this patent is extended or adjusted under 35 U.S.C. 154(b) by 1011 days.

(21) Appl. No.: 12/476,091

(22) Filed: Jun. 1, 2009

(65) Prior Publication Data

US 2010/0036258 A1  Feb. 11, 2010

Related U.S. Application Data (60) Provisional application No. 61/057,585, filed on May 30, 2008.

(51) Int. Cl.
*A61B 8/14* (2006.01)
*A61B 8/00* (2006.01)

(52) U.S. Cl.
USPC ............ 600/466; 600/463; 600/437; 600/459

(58) Field of Classification Search
USPC ........................................................ 600/466
See application file for complete search history.

(56) References Cited

U.S. PATENT DOCUMENTS

| | | | |
|---|---|---|---|
| 3,955,561 A | 5/1976 | Eggleton | |
| 4,059,098 A | 11/1977 | Murdock | |
| 4,092,867 A | 6/1978 | Matzuk | |
| 4,149,419 A | 4/1979 | Connell, Jr. et al. | |
| 4,316,271 A | 2/1982 | Evert | |
| 4,398,425 A | 8/1983 | Matzuk | |
| 4,399,703 A | 8/1983 | Matzuk | |
| 4,421,118 A | 12/1983 | Dow et al. | |
| 4,455,872 A | 6/1984 | Kossoff et al. | |
| 4,474,184 A | 10/1984 | Harui | |
| 4,664,121 A | 5/1987 | Sanghvi et al. | |
| 4,747,411 A | 5/1988 | Ledley | |
| 4,756,313 A | 7/1988 | Terwilliger | |
| 4,784,148 A | 11/1988 | Dow et al. | |
| 4,794,930 A | 1/1989 | Machida et al. | |
| 4,841,979 A | 6/1989 | Dow et al. | |
| 4,895,158 A | 1/1990 | Kawabuchi et al. | |
| 4,913,155 A * | 4/1990 | Dow et al. ..................... | 600/446 |
| 4,977,898 A | 12/1990 | Schwarzschild et al. | |

(Continued)

FOREIGN PATENT DOCUMENTS

EP  0982711  12/2008

*Primary Examiner* — Tse Chen
*Assistant Examiner* — Patricia Park
(74) *Attorney, Agent, or Firm* — Richard W. Ellis (57) ABSTRACT

An ultrasound catheter probe assembly capable of scanning a three-dimensional volume is provided. The ultrasound catheter probe assembly contains a plurality of ultrasonic transducers disposed along a central axis of the ultrasound catheter probe assembly. The plurality of ultrasonic transducers is disposed on a mechanism operable to reciprocally pivot the plurality of ultrasonic transducers enabling the plurality of ultrasonic transducers to scan a three-dimensional volume. A helically disposed electrical interconnection member may be disposed about a pivot axis of the plurality of ultrasonic transducers and may electrically interconnect the plurality of ultrasonic transducers to an ultrasound imaging system. The ultrasound transducer catheter probe assembly may be fluid-filled and contain bubble position control and fluid expansion compensation features.

28 Claims, 4 Drawing Sheets

U.S. PATENT DOCUMENTS

| | | |
|---|---|---|
| 5,070,879 A | 12/1991 | Herres |
| 5,152,294 A | 10/1992 | Mochizuki et al. |
| 5,159,931 A | 11/1992 | Pini |
| 5,226,422 A | 7/1993 | McKeighen et al. |
| 5,351,692 A | 10/1994 | Dow et al. |
| 5,379,772 A * | 1/1995 | Imran .......................... 600/463 |
| 5,402,789 A | 4/1995 | Dow et al. |
| 5,429,136 A * | 7/1995 | Milo et al. .................... 600/439 |
| 5,460,179 A | 10/1995 | Okunuki et al. |
| 5,486,162 A | 1/1996 | Brumbach |
| 5,531,119 A | 7/1996 | Meyers |
| 5,662,116 A | 9/1997 | Kondo et al. |
| 5,842,473 A | 12/1998 | Fenster et al. |
| 6,126,606 A | 10/2000 | Bergstoel |
| 6,213,948 B1 | 4/2001 | Barthe et al. |
| 6,461,298 B1 | 10/2002 | Fenster et al. |
| 7,494,469 B2 | 2/2009 | Bruestle |
| 2004/0006277 A1 | 1/2004 | Langenhove et al. |
| 2004/0204650 A1 | 10/2004 | Taylor |
| 2005/0015011 A1 | 1/2005 | Liard et al. |
| 2007/0167813 A1 | 7/2007 | Lee et al. |
| 2007/0167821 A1* | 7/2007 | Lee et al. ..................... 600/463 |
| 2007/0250000 A1* | 10/2007 | Magnin et al. ........... 604/103.04 |
| 2008/0033292 A1 | 2/2008 | Shafran |
| 2008/0097403 A1 | 4/2008 | Donaldson et al. |
| 2008/0287797 A1 | 11/2008 | Lee et al. |

* cited by examiner

REAL TIME ULTRASOUND CATHETER PROBE

RELATED APPLICATIONS

This application claims priority under 35 U.S.C. §119 to U.S. Provisional Patent Application Ser. No. 61/057,585, filed May 30, 2008, entitled "REAL TIME ULTRASOUND CATHETER PROBE", which is hereby incorporated by reference in its entirety.

BACKGROUND

Ultrasound imaging probes continue to enjoy widespread use in the medical field. Ultrasound probes are used in a wide variety of applications where it is desired to generate images of the internal structure of a patient. Additionally, ultrasound catheter probes are utilized for a wide variety of laparoscopic, endoscopic and intravascular imaging applications. The ultrasound images provided by imaging probes may, for example, be used for diagnostic purposes.

Ultrasound imaging probes typically include a plurality of parallel piezoelectric transducer elements arranged along a longitudinal axis, with each element interconnected to a pair of electrodes. By sequentially sending and receiving ultrasonic energy from each transducer element, the ultrasound imaging probe is operable to scan an imaging plane along the length of, and perpendicular to, the plurality of parallel piezoelectric transducer elements.

Ultrasound imaging probes capable of scanning three dimensions have been developed that scan a three-dimensional volume by reciprocally pivoting the plurality transducer elements arranged along the longitudinal axis, thus sweeping the imaging plane through the three-dimensional volume.

SUMMARY

As the applications for, and use of, ultrasound imaging probes capable of scanning three dimensions continue to expand, so does the need for ultrasound probe designs that yield higher imaging performance, greater miniaturization, greater robustness and/or increased production efficiencies. In this regard, the ability to realize enhanced performance, miniaturization, robustness and production efficiencies through improvements to component configuration, fluid pressure management, bubble management and array electrical interconnections used in ultrasound imaging catheter probes becomes particularly significant. As used herein, the term "catheter" includes a tubular medical device for insertion into canals, ducts, vessels, passageways, body cavities and/or any other appropriate structure of a patient to permit imaging of an internal volume of the patient. Typically, catheters are relatively thin and flexible to facilitate advancement/retraction along non-linear paths.

In view of the foregoing, an object of embodiments described herein may be to provide improved component configurations to yield, inter alia, greater overall compactness. An additional objective may be to provide improved fluid pressure management capability. Another objective may be to improve the management of bubbles that may form or enter into a fluid-filled portion of the imaging catheter probe such that the bubbles do not substantially interfere with imaging performance. A further objective may be to provide improved electrical interconnection members between the moving components of the imaging catheter probe (e.g., a transducer array) and the static components of the imaging catheter probe (e.g., the outer shaft).

One or more of the above-noted objectives and additional advantages may be realized by the ultrasound catheter probe comprising the present invention. The inventive ultrasound catheter probe may include a portion having an enclosed volume and an ultrasound transducer array disposed within the enclosed volume. In certain embodiments the ultrasound transducer array may include a fluid disposed within the enclosed volume. In such embodiments, the ultrasound transducer array may be immersed within the fluid to facilitate enhanced acoustic coupling upon insertion of the probe into a patient during imaging procedures. In certain embodiments the ultrasound transducer array may be disposed for reciprocal pivotal movement within the enclosed volume, thereby yielding real-time, three-dimensional images of internal body tissue. Such an arrangement may be configured for hand-held use of a portion of the ultrasound catheter probe external to the body of the patient while another portion of the ultrasound catheter probe may be disposed within the body of the patient for use in imaging an internal volume of the patient. The technician or other operator may hold the external portion of the ultrasound catheter probe while manipulating the probe relative to a volume of interest within the patient.

In one aspect, the ultrasound catheter probe may include a bellows member having a flexible, closed-end portion located within the fluid in the enclosed volume and an open-end isolated from the fluid, wherein the bellows member is collapsible and expansible in response to volumetric variations in the fluid. As may be appreciated, the provision of a bellows member may maintain operational integrity of the ultrasound transducer catheter probe when exposed to conditions that may cause a volumetric change in the contained fluid.

In one approach, the ultrasound catheter probe may include an internal portion of the catheter located adjacent to and sealably separated from the enclosed volume, wherein the open end of the bellows member is in open communication with the internal portion of the catheter for internal pressure equalization therebetween. The provision of internal portion of the catheter facilitates pressure equalization and offers protection in relation to the open end of the bellows member.

At least the closed end portion of the bellows member may be elastically deformable. In this regard, the closed end portion of the bellows member may be elastically expandable in response to volumetric variations in the fluid. The bellows member may be operable to maintain operational integrity of the ultrasound catheter probe despite fluid volume changes that may occur due to exposure of the ultrasound catheter probe to relatively warm or cool temperatures during, for example, transport and/or storage. Such an elastically expandable bellows member may be particularly advantageous with respect to low temperatures where the fluid typically contracts more than a case of the ultrasound catheter probe.

In another aspect, the ultrasound catheter probe may include a bubble-trap member fixedly positioned relative to the enclosed volume and a fluid disposed within the enclosed volume. The bubble-trap member may have a distal-facing concave surface, wherein a distal portion of the enclosed volume is defined distal to the bubble-trap member and a proximal portion of the enclosed volume is defined proximal to the bubble-trap member. The ultrasound transducer array may be located in the distal portion and an aperture may be provided through the bubble-trap member to fluidly connect the distal portion of the enclosed volume to the proximal portion of the enclosed volume. The ultrasound catheter probe may include a catheter shaft that includes an inner shaft and an outer shaft. The bubble-trap may be disposed within the inner shaft. The bubble-trap may be disposed proximate to a distal end of the inner shaft.

As may be appreciated, bubbles present in the contained fluid can negatively affect images obtained by the ultrasound transducer array and are undesired. In the described arrangement, the probe may be oriented with the proximal end upwards, wherein bubbles may be directed by the concave surface through the aperture of the bubble-trap, and effectively isolated from the ultrasound transducer array by virtue of the bubbles being trapped in the proximal portion of the enclosed volume by the bubble-trap. In another method of controlling bubble location, a user may grasp the catheter probe assembly at a point proximal to the enclosed volume and swing around the portion of the catheter probe assembly with the enclosed volume to impart centrifugal force on the fluid within the enclosed volume thereby causing the fluid to move toward the distal end and any bubbles within the fluid to move towards the proximal portion of the enclosed volume.

In an arrangement, a filter may be disposed across the aperture. The filter may be configured such that air may pass through the aperture while the fluid may be unable to pass through the aperture. The filter may include expanded polytetrafluoroethylene (ePTFE).

In an embodiment, the ultrasound transducer array may be disposed for reciprocal movement within the enclosed volume, and a gap between the ultrasound transducer array and an inner wall of the enclosed volume may be sized such that fluid is drawn into the gap via capillary forces. To achieve such a gap, the ultrasound transducer array may include a cylindrical enclosure disposed about the array and the gap may exist between the outer diameter of the cylindrical enclosure and the inner wall of the enclosed volume.

In an aspect, the ultrasound catheter probe may include a catheter having a portion having an enclosed volume, an ultrasound transducer array disposed for reciprocal pivotal movement about a pivot axis within the enclosed volume, and an electrical interconnection member having a first portion coiled (e.g., coiled in a single plane in a clock spring arrangement, coiled along an axis in a helical arrangement) within the enclosed volume and electrically interconnected to the ultrasound transducer array.

In an arrangement, the first portion of the electrical interconnection member may be helically disposed within the enclosed volume about a helix axis. As the transducer is pivoted, the helically wrapped first portion may tighten and loosen about the helix axis. The pivot axis may be coincident with the helix axis. The enclosed volume may be disposed at a distal end of the ultrasound catheter probe. A fluid may be disposed within the enclosed volume.

In another further aspect, the ultrasound transducer array may be disposed for reciprocal movement about a pivot axis within the enclosed volume. The ultrasound catheter probe may further include at least a first electrical interconnection member (e.g. for conveying ultrasound imaging signals to/from the ultrasound transducer array). The first electrical interconnection member may include a first portion coiled about the pivot axis and interconnected to the ultrasound transducer array.

In an embodiment, the first electrical interconnection member may include a second portion adjoining the first portion, wherein the second portion is fixedly positioned relative to a catheter shaft, and wherein upon reciprocal movement of the ultrasound transducer array, the coiled first portion of the first electrical interconnection member tightens and loosens about the pivot axis. The second portion of the first electrical interconnection member may be helically and fixedly positioned about an inner core member disposed within the catheter shaft.

In one approach, the first electrical interconnection member may be ribbon-shaped and may comprise a plurality of conductors arranged side-by-side with electrically non-conductive material disposed therebetween across the width of the member. By way of example, the first electrical interconnection member may comprise a GORE™ Microminiature Flat Cable available from WL Gore & Associates, Newark, Del., U.S.A, wherein the first portion of the first electrical interconnection member may be disposed so that a top or bottom side thereof faces and wraps about a pivot axis of an ultrasound transducer array.

In another embodiment, the first portion of the electrical interconnection member may be coiled a plurality of times about the pivot axis. More particularly, the first portion of the first electrical interconnection member may be helically disposed about the pivot axis a plurality of times. In one approach, the first electrical interconnection member may be helically disposed about the pivot axis in a non-overlapping manner, i.e. where no portion of the first electrical interconnection member overlies another portion thereof.

In another approach, the first electrical interconnection member may be ribbon-shaped and may be helically disposed about the pivot axis a plurality of times. Upon reciprocal pivotal movement of the ultrasound transducer array, the helically wrapped, ribbon shaped portion may tighten and loosen about the helix axis. The ultrasound catheter probe may further include a motor operable to produce the reciprocal pivotal movement. A flex board may be electrically interconnected to the ultrasound transducer array, and the flex board may electrically interconnect to the first electrical interconnection member at a location between the motor and an outer wall of the catheter. The interconnection between the flex board and the first electrical interconnection member may be supported by a cylindrical interconnection support.

The ultrasound catheter probe may have a round cross-sectional profile. The ultrasound catheter probe may include a sealable port. The sealable port may be used to fill the ultrasound catheter probe with fluid and then it may be sealed.

In an embodiment, the ultrasound catheter probe may include a motor disposed within the enclosed volume and operatively interconnected to the ultrasound transducer array. The motor drives the array for the reciprocal pivotal movement.

In an embodiment, the ultrasound catheter probe may include a lumen. The lumen may extend from the proximal end of the catheter probe assembly to at least the first electrical interconnection member. A portion of the lumen may be disposed within a coil of the first portion of the first electrical interconnection member.

The ultrasound catheter probe may be configured such that the ultrasound transducer array is disposed distally along the ultrasound catheter probe relative to the first portion of the first electrical interconnection member. In an alternate arrangement, the ultrasound catheter probe may be configured such that the first portion of the first electrical interconnection member is disposed distally relative to the ultrasound transducer array. In such an alternate arrangement, a portion of the first electrical interconnection member may be fixed relative to a case of the ultrasound catheter probe where the first electrical interconnection member passes the ultrasound transducer array. In either arrangement, the first portion may be coiled within the enclosed volume.

In an arrangement, the ultrasound catheter probe may include a driveshaft operatively interconnected to the ultrasound transducer array. The driveshaft may be operable to drive the array for the reciprocal pivotal movement. The driveshaft may extend from the proximal end of the ultrasound catheter probe to the ultrasound transducer array. The driveshaft may be driven by a motor.

In an embodiment, the first portion of the first electrical interconnection member may be disposed in a clock spring arrangement. A center line of the first portion of the first electrical interconnection member may be disposed within a single plane that is in turn disposed perpendicular to the pivot axis. The ultrasound catheter probe includes a distal end and a proximal end, and in an arrangement, the first portion (the clock spring) may be disposed closer to the distal end of the ultrasound catheter probe than the ultrasound transducer array. The first portion may comprise a flex board.

In an aspect, the ultrasound catheter probe may include a catheter, an ultrasound transducer array, and at least a first electrical interconnection member. The ultrasound catheter probe may have a portion having a first volume that may be open to an environment surrounding at least a portion of the ultrasound catheter probe. The ultrasound transducer array may be disposed for reciprocal pivotal movement about a pivot axis within the first volume. In this regard, the ultrasound transducer array may be exposed to fluid (e.g., blood) present in the environment surrounding the ultrasound catheter probe. The first electrical interconnection member may have a first portion coiled within the first volume and electrically interconnected to the ultrasound transducer array.

In an embodiment, the first portion of the first electrical interconnection member may be helically disposed within the first volume about a helix axis. The first electrical interconnection member may further include a second portion adjoining the first portion. The second portion may be fixedly positioned relative to a case partially surrounding the first volume. Upon the reciprocal pivotal movement, the coiled first portion of the first electrical interconnection member may tighten and loosen. The first electrical interconnection member may be ribbon-shaped and include a plurality of conductors arranged side-by-side with electrically non-conductive material therebetween.

An acoustic structure may at least partially surround the ultrasound transducer array. The acoustic structure may have a round cross-sectional profile. Such a profile may reduce turbulence in the surrounding blood, reduce damage to the surrounding blood cells, and aid in avoiding thrombogenicity while the array is undergoing reciprocal pivotal movement.

The first portion of the first electrical interconnection member may be disposed in a clock spring arrangement. The clock spring arrangement may be disposed within the first volume that may be open to the environment surrounding at least a portion of the ultrasound catheter probe.

In conjunction with the present invention, a number of inventive methods may be realized. For example, a method is provided for maintaining fluid pressure within an enclosed volume of a catheter probe having an ultrasound transducer array. The method may include locating a flexible bellows, wherein the flexible bellows includes a closed-end portion positioned in the fluid located within the enclosed volume, and an open-end thereof positioned in an isolated location from the fluid. The method may include collapsing the bellows member in response to a volumetric expansion of the fluid. The method may include expanding the bellows member in response to a volumetric contraction of the fluid. In conjunction with such method, the open-end of the bellows may be disposed in open communication with an interior portion of a catheter shaft adjacent to and sealably separate from the enclosed volume. In turn, the method may include equalizing internal pressure within the bellows member and the interior portion of the catheter shaft of the ultrasound catheter probe.

The various features discussed above in relation to each aforementioned aspect may be utilized by any of the aforementioned aspects. Additional aspects and corresponding advantages will be apparent to those skilled in the art upon consideration of the further description that follows.

DETAILED DESCRIPTION

Figure 1:
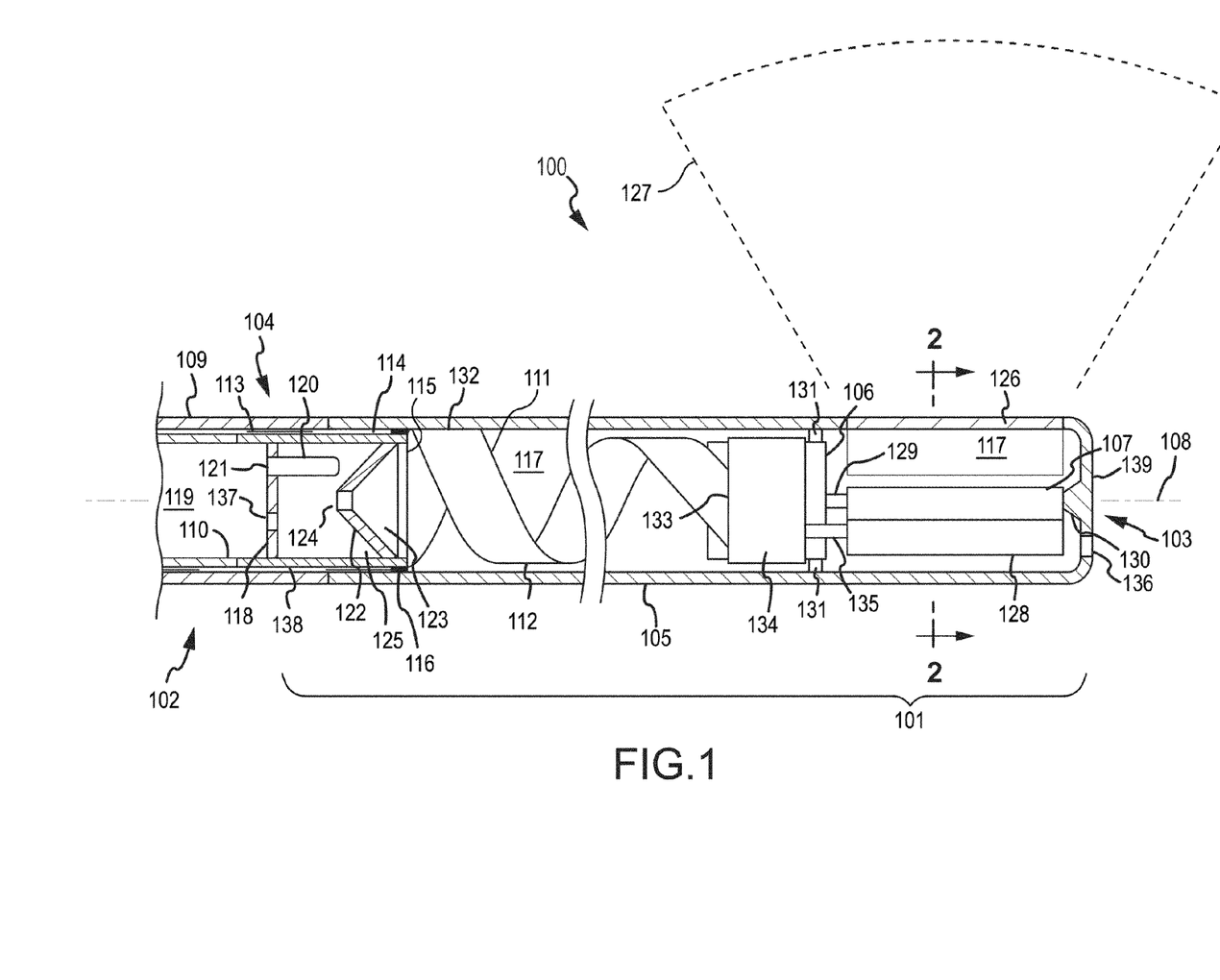
FIG. 1 is a partial cross-sectional view of an ultrasound catheter probe assembly.

FIG. 1 is a partial cross-sectional view an ultrasound catheter probe assembly 100. The catheter probe assembly 100 includes a catheter tip 101 attached to a catheter shaft 102. The catheter probe assembly 100 may generally be sized and shaped for insertion into a patient and subsequent imaging of an internal portion of the patient. The catheter probe assembly 100 may generally include a distal end 103 and a proximal end (not shown). The catheter probe assembly 100 proximal end may include a control device operable to be hand-held by a user (e.g., physician). The user may manipulate the movement of the catheter probe assembly 100 by manipulating the control device. During imaging, the distal end 103 of the catheter probe assembly 100 may be disposed within the body of a patient while the control device and the proximal end of the catheter probe assembly remain external to the patient.

The catheter tip 101 may be disposed between the distal end 103 and a proximal end 104 of the catheter tip 101. The catheter tip 101 may include a catheter tip case 105. The catheter tip case 105 may be a relatively rigid (as compared to the catheter shaft 102) member housing a motor 106 and a transducer array 107, both of which are discussed below. Alternatively, as noted below, a portion of the catheter tip case 105 may be steerable and/or flexible. The catheter tip 101 may include a central axis 108.

The catheter shaft 102 may be operable to be guided into the patient. The catheter shaft 102 may use any appropriate guidance method such as, but not limited to, a set of guide wires and associated controls. In this regard, the catheter shaft 102 may be steerable. The catheter shaft 102 may be flexible and therefore be operable to be guided through and follow contours of the structure of the patient, such as the contours of the vasculature system. The catheter shaft 102 may include an outer layer 109 and an inner layer 110. The outer layer 109 may be constructed from a single layer of material or it may be constructed from a plurality of distinct layers of materials. Similarly, the inner layer 110 may be constructed from a single layer of material or it may be constructed from a plurality of distinct layers of materials. The inner layer 110 includes a distal section 138 that is disposed at the distal end of the inner layer 115. The distal section 138 may be an integral part of the inner layer 110. Alternatively, the distal section 138 may be separate from the remainder of the inner layer 110 prior to assembly of the catheter probe assembly 100, and during assembly the distal section 138 may be interconnected to the remainder of the inner layer 110. The inner layer 110, the outer layer 109, or both may be configured and/or reinforced to mitigate unwanted catheter rotation due to reciprocal motion described herein and/or to generally increase the strength of the catheter probe assembly. Such reinforcement may take the form of a braided member disposed on or adjacent to the inner layer 110 and/or the outer layer 109.

An electrical interconnection member 111 may be disposed within the catheter probe assembly 100. The electrical interconnection member 111 may be comprised of a first portion 112 and a second portion 113. The second portion 113 of the electrical interconnection member 111 is illustrated in cross-section in FIG. 1. The first portion 112 of the electrical interconnection member 111 is not shown in cross-section in FIG. 1. The second portion 113 of the electrical interconnection member 111 may be disposed between the outer layer 109 and inner layer 110 along the catheter shaft 102. As illustrated the second portion 113 of the electrical interconnection member 111 may be helically disposed around the inner layer 110. The second portion 113 may be disposed in the region 114 between the inner layer 110 and outer layer 109. In another embodiment, the second portion 113 may be wrapped about and bonded to an inner core (not shown) that may be disposed within an internal portion 119 of the catheter shaft 102. The second portion 113 bonded to the inner core may be fixed relative to the inner layer 110 or it may float free from the inner layer 110. The second portion 113 bonded to the inner core may improve kink resistance and torque response of the catheter probe assembly 100. In such an embodiment, the second portion 113 may be bonded to the inner core and the first portion 112 may remain free from attachment to the inner core and the catheter tip case 105.

A distal end 115 of the inner layer 110 may be sealed along its outer perimeter using a sealing material 116. The sealing material 116 may be disposed as illustrated between the outer perimeter of the distal end 115 of the inner layer 110 and an inner surface of the catheter tip case 105. In another embodiment, the outer layer 109 of the catheter shaft 102 may extend to or beyond the distal end 115 of the inner layer 110 and in such an embodiment, the sealing material 116 may be disposed between the outer perimeter of the distal end 115 of the inner layer 110 and an inner surface of the outer layer 109. Alternatively, the region 114 between the inner layer 110 and the outer layer 109 may, in addition to containing the helically disposed second portion 113 of the electrical interconnection member 111, be partially or completely filled with the sealing material 116. The sealing material 116 may include any appropriate material such as, for example, a thermoset or thermoplastic material or expanded polytetrafluoroethylene (ePTFE). The second portion 113 of the electrical interconnection member 111 may extend along an entire length of the catheter shaft 102 from the proximal end 104 of the catheter tip 101 to an ultrasound imaging apparatus (not shown). In this regard, the electrical interconnection member 111 may operatively connect the catheter tip 101 with the ultrasound imaging apparatus.

An enclosed volume 117 may be defined by the catheter tip case 105, an end portion of the inner layer 110 of the catheter shaft 102 and an enclosed volume end wall 118. The enclosed volume end wall 118 may be sealably disposed within the inner layer 110 near to the distal end 115 of the inner layer 110. The enclosed volume 117 may also be sealed by the sealing material 116 as discussed above.

The enclosed volume 117 may be fluid-filled and sealed. The fluid may be a biocompatible oil selected, inter alia, for its acoustical properties. For example, the fluid may be chosen to match or approximate the acoustic impedance and/or the acoustic velocity of fluid within the region of the body that is to be imaged. The enclosed volume 117 may be sealed such that the fluid within the enclosed volume 117 is substantially unable to leak out of the enclosed volume 117. Furthermore, the enclosed volume 117 may be sealed to substantially prevent gasses (e.g., air) from entering into the enclosed volume 117.

The catheter probe assembly 100 may be filled using any appropriate method. During filling, the catheter probe assembly 100 and the fluid may be at known temperatures to beneficially control the volume of fluid introduced and the size of the enclosed volume 117. In one exemplary filling method, the catheter tip case 105 may include a sealable port 136. Gasses within the enclosed volume may be drawn by vacuum out of the enclosed volume 117 through the sealable port 136. Then, the fluid may be introduced through the sealable port 136 until the desired amount of fluid is within the enclosed volume 117. The sealable port 136 may then be sealed. In another example, the catheter probe assembly 100 may include the sealable port 136 at the distal end 103 and a sealable port 137 at the proximal end 104. The sealable port 137 may be disposed along the enclosed volume proximal end wall 118. One of the ports 137, 138 may be used as an inlet port for the fluid while the other port 137, 138 may be used as an outlet port for displaced gasses. In this regard, as fluid is passed through the inlet port, gasses may escape (or be pulled from using a vacuum) from the enclosed volume 117 through the outlet port. Once the desired volume of fluid is within the enclosed volume 117, the ports 137, 138 may be sealed. In the above described filling methods, a measured amount of fluid may be removed from the enclosed volume 117 after it has been completely filled. The amount of fluid removed may correspond to the desired amount of expansion of a bellows member 120 (described below).

The catheter tip 101 may include a check valve (not shown) that may be operable to allow fluid to flow out of the enclosed volume 117 if the pressure differential between the enclosed volume 117 and the surrounding environment exceeds a predetermined level. The check valve may be in the form of a slit valve disposed along the catheter tip case 105. In this regard, the check valve may operate to relieve excess pressure that may be created during the filling process, thereby reducing the possibility of the catheter probe assembly 100 bursting during the filling procedure. Once the enclosed volume is filled, the check valve may be permanently sealed. For example, a clamp may be placed over the check valve to seal the check valve.

The internal portion 119 of the catheter shaft 102 may be sealably separated from the enclosed volume 117. The internal portion 119 of the catheter shaft 102 may be disposed within an interior volume of the inner layer 110. The internal portion 119 of the catheter shaft 102 may contain air and may be vented such that the pressure within the internal portion 119 of the catheter shaft 102 is equal or close to the local atmosphere pressure in which the catheter probe assembly 100 is situated. Such venting may be accomplished through a dedicated vent mechanism (such as an opening in the catheter shaft 102 at a point outside of the body of the patient) between the internal portion 119 of the catheter shaft 102 and the local atmosphere.

As may be appreciated, if the enclosed volume 117 was completely surrounded by substantially rigid members and filled with fluid, temperature variations of the catheter probe assembly 100 could result in unwanted changes in pressure within the enclosed volume 117. For example, in such a configuration, if the catheter probe assembly 100 was exposed to elevated temperatures, the pressure of the fluid within the enclosed volume 117 may increase; possibly causing some of the fluid to leak out of the enclosed volume 117. Likewise for example, if the catheter probe assembly 100 was exposed to reduced temperatures, the pressure of the fluid within the enclosed volume 117 may decrease, possibly causing some air or other fluid to leak into the enclosed volume 117. Accordingly, it may be beneficial to prevent or reduce pressure variations within the enclosed volume 117 relative to the environmental conditions in which the catheter probe assembly 100 is located.

To assist in equalizing pressure between the fluid within the enclosed volume 117 and surrounding conditions, the bellows member 120 may be incorporated into the catheter probe assembly 100. The bellows member 120 may be a generally flexible member that is collapsible and expansible in response to volumetric changes in the fluid within the enclosed volume 117, such as volumetric changes as a result of temperature changes. The bellows member 120 may be configured to define an internal volume and have a single opening. The single opening may be an open end 121 of the bellows member 120 such that the open end 121 may be disposed along the end wall 118 and oriented such that the internal volume of the bellows member 120 is in communication with the internal portion 119 of the catheter shaft 102. The remaining portion of the bellows member 120 may be disposed within the enclosed volume 117 and may include a closed end portion.

The initial configuration of the bellows member 120 may be selected such that the bellows member 120 is operable to compensate for (e.g., equalize pressure between the enclosed volume 117 and the internal portion 119 of the catheter shaft 102) temperature variations across the operational range of temperatures for the catheter probe assembly 100. Moreover, the bellows member 120 may be configured to compensate for temperature variations greater than the operational range of temperatures for catheter probe assembly 100, such as temperature variations that may be seen during catheter probe assembly 100 storage and/or transportation. The bellows member 120 may be curved or otherwise shaped to avoid other internal components within the enclosed volume 117.

At the maximum fluid temperature for which the bellows member 120 is designed to compensate, the bellows member 120 may be totally collapsed or close to being totally collapsed. In this regard, the expansion of the fluid within the enclosed volume 117 may not result in a pressure increase within the enclosed volume 117 since the bellows member 120 collapse may compensate for the expansion of the fluid. At the minimum fluid temperature for which the bellows member 120 is designed to compensate, the bellows member 120 may be expanded at or near its expansion limit. In this regard, the volumetric contraction of the fluid within the enclosed volume 117 may not result in a pressure decrease within the enclosed volume 117 since the bellows member 120 expansion may compensate for the contraction of the fluid. Furthermore, by positioning the bellows member 120 in the enclosed volume 117, it is protected from movement of the catheter shaft 102.

Although the bellows member 120 is illustrated as having a cross dimension considerably smaller than a cross dimension of the inner layer of the catheter shaft 110, the bellows member 120 may be considerably larger. In this regard, the bellows member 120 may have a cross dimension approaching that of the inner layer of the catheter shaft 110. It will be appreciated that such a bellows member may be relatively less flexible than the bellows member 120 illustrated in FIG. 1, but may be similarly capable of accommodating fluid volume changes due to its relatively larger size. Such a larger bellows member may be constructed similarly to the inner 110 and/or outer 109 layers of the catheter shaft.

In conjunction with, or in place of, the bellows member 120, a portion of the sidewall of the catheter tip case 105 (e.g., a portion an end wall 139 of the catheter tip case 105 and/or a portion of the sidewall of the of the catheter tip case 105 proximate to the first portion of the electrical interconnect member 112) may be configured such that the portion performs a function similar to that of the bellows member 120 described above. For example, the portion may be pliable and may flex inward if the fluid and catheter probe assembly 100 become cooler and outward if the fluid and catheter probe assembly 100 become warmer, thereby accommodating temperature related volume changes of the fluid.

In an embodiment, the bellows member 120, or at least a distal portion thereof, may be elastically-deformable. In particular, the bellows member 120 may be operable to stretch or elastically expand beyond a neutral state (e.g., a state where there is no pressure differential between the inside of the bellows member 120 and the outside of the bellows member 120) in reaction to a pressure differential between the enclosed volume 117 and the interior of the catheter 119 where the pressure within the interior of the catheter 119 is greater than the pressure within the enclosed volume 117. Such stretching or elastic expansion may accommodate greater pressure differentials than would be attainable with a similarly sized bellows member 120 that was substantially incapable of stretching or elastically expanding. Furthermore, such a stretchable or elastically expandable bellows member 120 may result in a catheter probe assembly 100 that is capable of tolerating temperature variations greater than the operational range of temperatures for the catheter probe assembly 100, such as temperature variations that may be seen during catheter probe assembly 100 storage and/or transportation. Such a stretchable or elastically expandable bellows member 120 may be capable of withstanding a greater range of fluid volumes (e.g., the catheter probe assembly 100 with a stretchable or elastically expandable bellows member 120 may be more tolerant of a wider range of ambient temperatures, extending particularly the low temperature range where the fluid typically contracts more than the catheter tip case 105). Such a stretchable or elastically expandable bellows member 120 may be silicone based and may be produced using, for example, a liquid transfer molding process.

In one embodiment, a resilient, elastically-deformable bellows member 120 may be provided so that in a neutral state the bellows member 120 automatically assumes an initial configuration. Such initial configuration may correspond with a preformed configuration (e.g. a bulbous, dropper-shaped configuration), except as spatially restricted by other rigid componentry (e.g., bubble trap 122 and/or enclosed volume proximal end wall 118). In turn, the bellows member 120 may collapse and automatically expand and stretch relative to such initial configuration in response to pressure variations.

The catheter probe assembly may include a bubble-trap 122, shown in cross section in FIG. 1. The bubble-trap 122 may be interconnected to the distal end 115 of the inner layer 110 of the catheter shaft 102. The bubble-trap 122 may be interconnected to the inner layer 110 by any appropriate means. For example, the bubble-trap 122 may be bonded to the inner layer 110 using an adhesive. For example, the bubble trap 122 may be press-fit into the inner layer 110.

The bubble-trap 122 may include a recess defined by a distal-facing concave surface 123. Furthermore, a distal portion of the enclosed volume 117 is defined as the portion of the enclosed volume 117 distal to the bubble-trap 122. Correspondingly, a proximal portion of the enclosed volume 117 is defined as the portion of the enclosed volume 117 proximal to the bubble-trap 122. The bubble-trap 122 may include an aperture 124 that fluidly interconnects the distal portion to the proximal portion. The aperture 124 may be disposed at or near the most proximal portion of the distal facing concave surface 123.

During the life cycle of the catheter probe assembly 100, bubbles may be formed in or enter into the enclosed volume 117. The bubble-trap 122 may be operable to trap these bubbles in the proximal portion of the enclosed volume 117. For example, during normal operation of the catheter probe assembly 100 the catheter probe assembly may be disposed in a variety of attitudes including attitudes where the distal end 103 of the catheter probe assembly 100 is facing downward. When the catheter probe assembly 100 is in a downward facing attitude, a bubble within the distal portion may tend to naturally flow upward. Upon coming into contact with the concave face 123, the bubble may continue to rise until it reaches the aperture 124. The bubble may then pass through the aperture 124, moving from the distal portion to the proximal portion. Once the bubble is in the proximal portion and the catheter probe assembly 100 is placed in an attitude where the distal portion is facing upward, the bubble-trap 122 will tend to direct any rising bubbles in the proximal portion away from the aperture 124. Following the slope of the proximal surface of the bubble-trap 122, the bubbles will tend to migrate to a trap region 125 and be trapped therein.

The bubble-trap 122 is beneficial since bubbles present between the transducer array 107 and an acoustic window 126 of the case 105 may produce unwanted image artifacts when the catheter probe assembly 100 is used to generate an image of an image volume 127. This is due to the differing acoustical properties of an air bubble versus the acoustical properties of the fluid within the enclosed volume 117. By keeping bubbles that may form during the lifetime of the catheter probe assembly 100 away from the transducer array 107, the operational life of the catheter probe assembly 100 may be increased. In this regard, bubbles that may form within the enclosed volume 117 or enter into the enclosed volume 117 may not lead to a degradation of the images created using the catheter probe assembly 100.

Prior to insertion of the catheter probe assembly 100 into a patient, a user (e.g., a physician or technician) may manipulate the catheter probe assembly 100 in a manner to help move any bubbles that may be present within the enclosed volume 117 into the volume proximal to the bubble trap 122. For example, the user may dispose the catheter probe assembly 100 in an attitude where the distal end 103 is pointing downward to allow bubbles within the enclosed volume 117 to move upward into the volume proximal to the bubble trap 122 thus trapping the bubbles. In another example, the user may grasp the catheter probe assembly 100 at a point proximal to the catheter tip 101 and swing the catheter tip 101 around to impart centrifugal force on the fluid within the enclosed volume 117 thereby causing the fluid to move toward the distal end 103 and any bubbles within the fluid to move towards the proximal end 104. In addition, the catheter probe assembly 100 may be packaged such that the distal end 103 is pointing downward so that any bubbles within the enclosed volume 117 may migrate to the proximal end 104 of the catheter tip 101 while the catheter probe assembly 100 is in storage or is being transported prior to use.

A filter may be disposed across the aperture 124. The filter may be configured such that gasses (e.g., air) may pass through the filter while liquid (e.g., oil, saline) may not be able to pass through the filter. Such a configuration may allow air bubbles to pass from the distal end of the enclosed volume 117 (the portion of the enclosed volume to the right of the bubble trap 122 in FIG. 1), through the filter disposed across the aperture 124, and into the proximal end of the enclosed volume 117 (the portion of the enclosed volume to the left of the bubble trap 122 in FIG. 1), while preventing fluid from passing through the filter disposed across the aperture 124. The filter may include ePTFE.

The catheter probe assembly 100 includes the transducer array 107 and an array backing 128. The transducer array 107 may comprise an array of a plurality of individual transducer elements that may each be electrically connected to the ultrasound imaging apparatus via a signal connection and a ground connection. The transducer array 107 may be a one-dimensional array that includes a single row of individual transducer elements. The transducer array 107 may be a two-dimensional array that includes individual transducer elements arranged, for example, in multiple columns and multiple rows. Ground connections of the entire transducer array 107 may be aggregated and may be electrically connected to the ultrasound imaging apparatus through a single ground connection. The transducer array 107 may be a mechanically active layer operable to convert electrical energy to mechanical (e.g., acoustic) energy and/or convert mechanical energy into electrical energy. For example, the transducer array 107 may comprise piezoelectric elements. For example, the transducer array 107 may be operable to convert electrical signals from the ultrasound imaging apparatus into ultrasonic acoustic energy. Furthermore, the transducer array 107 may be operable to convert received ultrasonic acoustic energy into electrical signals.

The transducer array may include a cylindrical enclosure disposed about the array 107 and array backing 128. The cylindrical enclosure may reciprocally pivot along with the array 107 and array backing 128. The cylindrical enclosure may be constructed of a material that has an acoustic speed similar to blood or other body fluid in which the catheter probe assembly 100 is to be inserted. The cylindrical enclosure may be sized such that a gap exists between the outer diameter of the cylindrical enclosure and the inner diameter of the case 105 and acoustic window 126. The gap may be sized such that capillary forces draw the fluid into, and keep the fluid within, the gap. The fluid may be the aforementioned oil, saline, blood (e.g., where the enclosed volume 117 is open to its surroundings), or any other appropriate fluid. In one embodiment, the fluid may be placed into the enclosed volume 117 at the time the catheter probe assembly 100 is manufactured. In a variation, the fluid may be added at the time of use of the catheter probe assembly 100.

To generate an ultrasound image, the ultrasound imaging apparatus may send electrical signals to the transducer array 107 which in turn may convert the electrical energy to ultrasonic acoustic energy that may be emitted toward the image volume 127. Structure within the image volume 127 may reflect a portion of the acoustic energy back toward the transducer array 107. The reflected acoustic energy may be converted to electrical signals by the transducer array 107. The electrical signals may be sent to the ultrasound imaging apparatus where they may be processed and an image of the image volume 127 may be generated.

Figure 2:
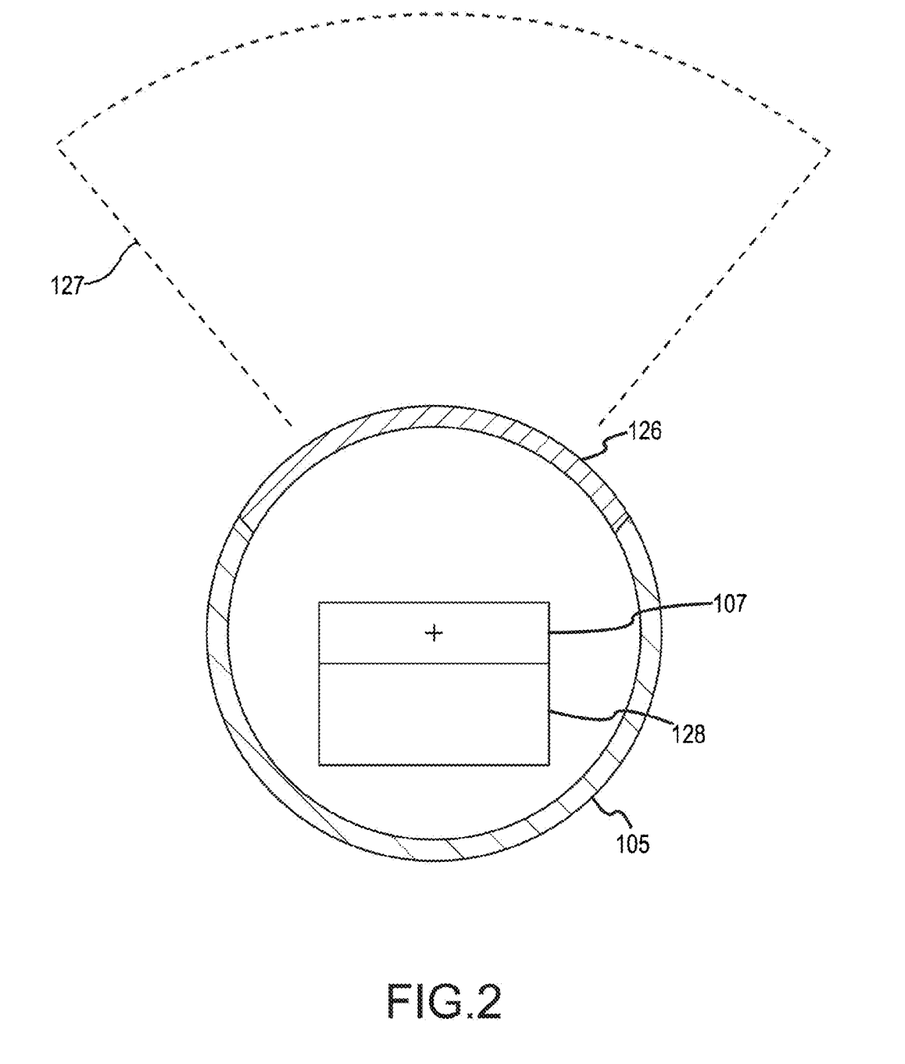
FIG. 2 is another partial cross-sectional view the ultrasound catheter probe assembly of FIG. 1.

Generally, the transducer array 107 is operable to transmit ultrasonic energy through the acoustic window 126 of the catheter tip case 105. In the catheter probe assembly 100, the acoustic window 126 forms part of the catheter tip case 105 along a portion of the circumference of the case along a portion of the length of the case. FIG. 2 is a cross sectional view of the catheter probe assembly 100 looking distally from section lines 2-2 of FIG. 1. As shown in FIG. 2, the acoustic window 126 forms a portion of the circumference of the catheter tip case 105 along section lines 2-2. The acoustic window 126 may, for example, occupy 90 degrees or more of the circumference of the catheter tip case 105. The acoustic window may comprise, for example, polyurethane, polyvinyl acetate, or polyester ether. The ultrasonic energy, in the form of acoustic waves, may be directed through the acoustic window 126 and into the internal structure of the patient.

As shown in FIG. 2, the catheter tip case 105 may have a generally circular cross section. Moreover, the outer surface of the catheter tip case 105 and the acoustic window 126 may be smooth. Such a smooth, circular exterior profile may help in reducing thrombogenicity and/or tissue damage as the catheter probe assembly 100 is moved (e.g., rotated, translated) within a patient.

In general, the images generated by the catheter probe assembly 100 may be of a subject (e.g., internal structure of a patient) within the image volume 127. The image volume 127 extends outwardly from the catheter probe assembly 100 perpendicular to the transducer array 107. The entire image volume 127 may be scanned by the transducer array 107. The plurality of ultrasonic transducers may be disposed along the central axis 108 and may be operable to scan an image plane with a width along the central axis 108 and a depth perpendicular to the transducer array 107. The transducer array 107 may be disposed on a mechanism operable to reciprocally pivot the transducer array 107 about the central axis 108 such that the image plane is swept about the central axis 108 to form the image volume as shown in FIGS. 1 and 2. The sweeping of the image plane about the central axis 108 enables the transducer array 107 to scan the entire image volume 127 and thus a three dimensional image of the image volume 127 may be generated. The catheter probe assembly 100 may be operable to reciprocally pivot the transducer array 107 at a rate sufficient enough to generate real-time or near real-time three-dimensional images of the image volume 127. In this regard, the ultrasound imaging apparatus may be operable to display live or near-live video of the image volume. Imaging parameters within the image volume 127, for example focal length and depth of field, may be controlled through electronic means known to those skilled in the art.

As noted above, the enclosed volume 117 may be fluid-filled. The fluid may act to acoustically couple the transducer array 107 to the acoustic window 126 of the catheter tip case 105. In this regard, the material of the acoustic window 126 may be selected to correspond to the acoustic impedance and/or the acoustic velocity of the fluid of the body of the patient in the region where the catheter tip 101 is to be disposed during imaging.

The transducer array 107 may be interconnected to an output shaft 129 of the motor 106 at a proximal end of the transducer array 107. Furthermore, the transducer array 107 may be supported on a distal end of the transducer array 107 by a pivot 130. As illustrated in FIG. 1, the pivot 130 may be a portion of the catheter tip case 105 that extends toward the transducer array 107 along the rotational axis (e.g., the central axis 108) of the transducer array 107. The transducer array 107 may have a corresponding recess or pocket along its distal end to receive a portion of the pivot 130. In this regard, the interface between the pivot 130 and the transducer array 107 may allow for the transducer array 107 to reciprocally pivot about its rotational axis while substantially preventing any lateral movement of the transducer array 107 relative to the catheter tip case 105. Accordingly, the transducer array 107 may be operable to be reciprocally pivoted about its rotational axis.

The motor 106 may be disposed within the enclosed volume 117. The motor 106 may be an electrically powered motor operable to rotate the output shaft 129 in both clockwise and counterclockwise directions. In this regard, the motor 106 may be operable to reciprocally pivot the output shaft 129 of the motor 106 and therefore reciprocally pivot the transducer array 107 interconnected to the output shaft 129.

The motor 106 may have an outer portion that has an outer diameter that is smaller than the inner diameter of the catheter tip case 105 in the region of the catheter tip case 105 where the motor 106 is disposed. The outer portion of the motor 106 may be fixedly mounted to the inner surface of the catheter tip case 105 by one or more motor mounts 131. The motor mounts 131 may, for example, be comprised of beads of adhesive. The motor mounts 131 may be disposed between the motor 106 and inner surface of the catheter tip case 105 in locations chosen to avoid interference with moving members (discussed below) associated with the reciprocal motion of the transducer array 107. Motor mounts 131 may be disposed along the distal end of the outer portion of the motor 106. Motor mounts 131 may also be disposed along the proximal end of the outer portion of the motor 106 such as, for example, along the proximal end of the outer portion of the motor 106 on the side of the motor 106 opposite from the side visible in FIG. 1.

When output shaft 129 position is known, the corresponding position of the transducer array 107 will be known. Output shaft 129 position may be tracked in any appropriate manner, such as through the use of an encoder and/or a magnetic position sensor. Output shaft 129 position may also be tracked through the use of hard stops limiting the motion of the transducer array 107. Such hard stops (not shown) may limit the range through which the transducer array 107 may reciprocally pivot. By driving the motor 106 in a clockwise or counterclockwise direction for a specific period of time, it may be assumed that the motor 106 has driven the transducer array 107 against one of the hard stops and therefore the position of the transducer array 107 may be known.

Electrical interconnections to the motor 106 from the ultrasound imaging apparatus may be achieved through a dedicated set of electrical interconnections (e.g., wires) separate from the electrical interconnection member 111. Alternatively, electrical interconnections to the motor 106 may be made using a portion of the conductors of the electrical interconnection member 111. Where a dedicated set of electrical interconnections are used to communicate with and/or drive the motor 106, such interconnections may be run from the motor 106 to the ultrasound imaging apparatus in any appropriate manner including, for example, through the interior 119 of the catheter shaft 102 and/or through the gap 114. Furthermore, electrical interconnections from the ultrasound imaging apparatus to other components, such as thermocouples, other sensors, or other members that may be disposed within the catheter tip 101, may be achieved through a dedicated set of electrical interconnections or they may be made using a portion of the conductors of the electrical interconnection member 111.

The electrical interconnection member 111 may electrically interconnect the transducer array 107 with the ultrasound imaging apparatus. The electrical interconnection member 111 may be a multi-conductor cable comprising of a plurality of conductors arranged side-by-side with electrically nonconductive material between the conductors. The electrical interconnection member 111 may be ribbon shaped. For example, the electrical interconnection member 111 may comprise one or more GORE™ Microminiature Flat Cables. For example, the electrical interconnection member 111 may include 64 separate conductors.

The electrical interconnection member 111 may be anchored such that a portion of it is fixed relative to the catheter tip case 105. As noted above, the second portion 113 of the electrical interconnection member 111 may be secured between the inner layer 110 and outer layer 109 of the catheter shaft 102. Within the enclosed volume 117, a first end 132 of the first portion 112 of the electrical interconnection member 111 may be secured to the inner surface of the catheter tip case 105. In this regard, the securing of the first end 132 may be configured such that the transition from a secured portion of the electrical interconnection member 111 to a free floating portion may be disposed perpendicular to the orientation of the conductors (e.g., across the width of the electrical interconnection member 111) at the first end 132. In another embodiment, the electrical interconnection member may be secured to the inner surface of the case by virtue of its securement between the inner layer 110 and outer layer 109 of the catheter shaft 102. In such an embodiment, the transition from secured to free floating may not be oriented perpendicular to the conductors of the electrical interconnection member 111. Any appropriate method of anchoring the electrical interconnection member 111 to the catheter tip case 105 may be used. For example, adhesive may be used.

Since during scanning the transducer array 107 may be pivoted about the central axis 108 relative to the catheter tip case 105, the electrical interconnection member 111 must be operable to maintain an electrical connection to the transducer array 107 while the transducer array 107 is pivoting relative to the catheter tip case 105 to which the electrical interconnection member 111 is fixed at the first end 132. This may be achieved by coiling the first portion 112 of the electrical interconnection member 111 within the enclosed volume 117. The first end 132 of the coil may be anchored as discussed. A second end 133 of the coil may be anchored to an interconnection support 134 that pivots along with the transducer array 107 about the central axis 108. Where the electrical interconnection member 111 is ribbon shaped, the first portion 112 of the electrical interconnection member 111 may be disposed such that a top or bottom side of the ribbon faces and wraps about the central axis 108.

FIG. 1 illustrates a configuration where the first portion 112 of the electrical interconnection member 111 is helically disposed within the enclosed volume 117. The first portion 112 of the electrical interconnection member 111 may be coiled about the central axis 108 a plurality of times. The first portion 112 of the electrical interconnection member 111 may be coiled about the central axis 108 such that the first portion 112 of the electrical interconnection member 111 forms a helix about the central axis 108. By coiling the electrical interconnection member 111 about the central axis 108 a plurality of times, undesirable counteracting torque on the pivoting of the transducer array 107 may be significantly avoided. Pivoting of the transducer array 107 about the central axis 108 in such a configuration may result in a slight tightening, or slight loosening, of the turns of the coiled first portion 112 of the electrical interconnection member 111. Such a slight tightening and loosening may result in each coil (e.g., each individual rotation of the helix about the central axis 108) producing only a small lateral displacement and corresponding displacement of fluid. Furthermore, the displacement may not be uniform for each coil of the helix. Furthermore, by distributing the movement of the first portion 112 of the electrical interconnection member 111 over a plurality of coils, the mechanical stresses of movement are distributed over the entire helically disposed first portion 112. Distributing mechanical stresses may result in longer mechanical life for the electrical interconnection member 111. The helically disposed first portion 112 of the electrical interconnection member 111 may be helically disposed in a non-overlapping manner (e.g., no portion of the electrical interconnection member 111 may overlie itself in the region of the helix). It will be appreciated that in another embodiment, the pivot axis of the transducer array 107 and accompanying structure may be offset from the central axis 108. It will be further appreciated that in various embodiments, the axis of the helix, the pivot axis of the transducer array 107, and the central axis 108 may all be offset from each other, may all be coincidental, or two of the axes may be coincidental and offset from the third.

The electrical interconnection member 111 may include ground and base layers. The ground and base layers may be configured differently than the other conductors of the electrical interconnection member 111. For example, the ground layer may be in the form of a plane extending across the width of the electrical interconnection member 111 and extending along the entire length of the electrical interconnection member 111. Along the first portion of the electrical interconnection member 112, the ground layer and/or the base layer may be separated from the remainder of the first portion of the electrical interconnection member 112. Accordingly, the ground layer and/or base layer may be in the form of separate conductors (not shown) between the first end 132 and the interconnection support 134. Such an arrangement may result in a more flexible structure than that illustrated in FIG. 1 where the first portion of the electrical interconnection member 112 includes the ground and base layers.

The first portion of the electrical interconnection member 112 disposed within the enclosed volume 117 may include additional layers of insulation relative to the second portion 113. Such additional layers may provide protection against the fluid occupying the enclosed volume and/or such additional layers may provide protection against wear due to the first portion of the electrical interconnection member 112 contacting other components (e.g., the case 105). The additional layers may, for example, be in the form of one or more coatings and/or laminates.

The portion of the case 105 that surrounds the enclosed volume 117 in the region of the first portion of the electrical interconnection member 112 may be structurally reinforced to resist kinking. Such reinforcement may be in the form of additional layers laminated to the inner and/or outer surface of the case 105 or in the form of a structural support member secured to the case 105.

In an embodiment, the first portion 112 of the electrical interconnection member 111 may include a total of about three revolutions about the central axis 108. The total length of the catheter tip case 105 may be selected to accommodate the number of revolutions needed for the first portion 112 of the electrical interconnection member 111. The total number of helical revolutions for the first portion 112 of the electrical interconnection member 111 may be determined based at least partially on desired coil expansion and contraction during pivotal movement, the desired level of counteracting torque imparted on the motor 106 by the first portion 112 during reciprocal movement, and the desired overall length of the catheter tip case 105. Within the enclosed volume 117, the first portion 112 of the electrical interconnection member 111 may be helically disposed such that there is a clearance between the outer diameter of the helix of the first portion 112 and the inner surface of the catheter tip case 105 as shown in FIG. 1.

The helically disposed first portion 112 of the electrical interconnection member 111 may be disposed such that a volume within the helically disposed first portion 112 may contain a tube or other component with a lumen therethrough or other appropriate component. Such lumens may accommodate any appropriate use such as, for example, catheter insertion, drug delivery, and/or guide wire following. For example, a tube with a lumen therethrough may be disposed within the helically disposed first portion 112. Such a tube may extend form the proximal end of the catheter probe assembly 100, pass through the enclosed volume end wall 118 (in embodiments including the enclosed volume end wall 118) and past the bubble trap 122 (in embodiments including the bubble trap 122). In such an embodiment, the bubble trap 122 may be offset from the central axis 108 to accommodate the tube. A portion of such a lumen may extend through at least a portion of the first portion of the electrical interconnection member 112. In an embodiment, the tube and lumen may terminate in a side port. For example, the lumen may terminate at the sidewall of the case in the region where the helically disposed first portion 112 is located.

The interconnection support 134 may serve to support an interconnection between the electrical interconnection member 111 and a flex board 135. As noted, the second end 133 of the first portion 112 of the electrical interconnection member 111 may be fixedly secured to the interconnection support 134. Additionally, the flex board 135 may be fixedly secured to the interconnection support 134. The individual conductors of the electrical interconnection member 111 may be electrically connected to individual conductors of the flex board 135. The flex board 135 may serve to electrically interconnect the electrical interconnection member 111 to the transducer array 107. Insulative material may be disposed over the electrical interconnections between the electrical interconnection member 111 and the flex board 135. The insulative material may be laminated over the electrical interconnections. In another embodiment, a rigid interconnection member may be used in place of the above-described flex board 135. Such a rigid interconnection member may serve to electrically interconnect the electrical interconnection member 111 to the transducer array 107.

The interconnection support 134 may be configured as a hollow cylinder operable to be disposed about the outer surface of the motor 106. Alternatively, the interconnection support 134 may be configured as a curved plane that is not wrapped completely around the outer surface of the motor 106. In either circumstance (e.g., hollow cylinder or curved plane), the interconnection support 134 may be operable to rotate about a portion of the outer surface of the motor 106. In this regard, as the motor 106 reciprocally pivots the transducer array 107, the transducer array backing 128 by virtue of its fixed connection to the transducer array 107 will also reciprocally pivot. In turn, by virtue of its fixed connection to the transducer array backing 128, the flex board 135 will also reciprocally pivot. In turn, by virtue of their fixed connection to the flex board 135, the interconnection support 134 and the second end 133 of first portion 112 the electrical interconnection member 111 will also reciprocally pivot along with the transducer array 107.

In another embodiment, the interconnection support 134 and the flex board 135 may be constructed from a single flex board. In such an embodiment, the interconnection support 134 portion of the single flex board may be formed into at least a portion of a cylinder such that it may be disposed at least partially about the outer surface of the motor 106.

Although the transducer array 107 and associated members are generally described herein as being disposed in a catheter tip 101 at a distal end 103 of the catheter probe assembly 100, other configurations are contemplated. For example, in another embodiment, the members disposed within the catheter tip 101 may be disposed at a point along the catheter shaft 102 that is offset from the distal end 103 of the catheter probe assembly 100. In this regard, portions of the catheter shaft 102 and/or other components may be disposed distal to the catheter tip 101.

In an alternate embodiment, the catheter tip case 105 may be in the form of a protective cage disposed about the electrical interconnection member 111, motor 106, array 107, and other appropriate components of the catheter probe assembly 100. Such a cage may allow blood (or other bodily fluid) into the volume corresponding to the enclosed volume 117 of the embodiment of FIG. 1. Such an embodiment would not require the bellows member 120 or the bubble trap 122. The cage may be open enough to allow blood to flow throughout the volume corresponding to the enclosed volume 117, yet have enough structure to assist in protecting blood vessels and/or other patient structures from damage from contact with the catheter probe assembly 100. Moreover, in such an embodiment an acoustic structure may be interconnected to the array 107. The acoustic structure may be made from a material or materials selected to maintain the imaging capabilities of the array 107. The acoustic structure may be rounded in cross section to reduce turbulence in the surrounding blood, reduce damage to the surrounding blood cells, and aid in avoiding thrombogenicity while the array is undergoing reciprocal pivotal movement. Other components may also be shaped to help reduce turbulence, avoid thrombogenicity, and avoid damage to blood cells.

Figure 3:
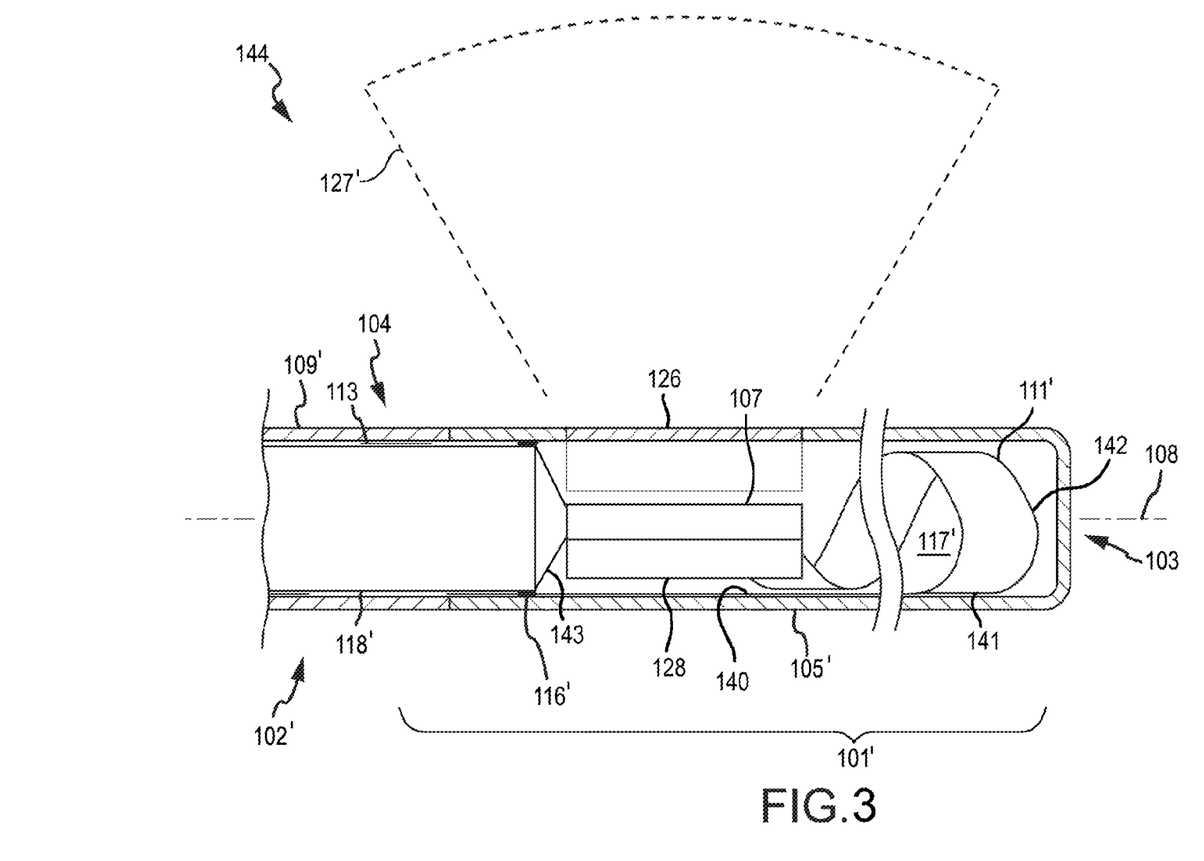
FIG. 3 is a partial cross-sectional view of an ultrasound catheter probe assembly.

FIG. 3 is a partial cross-sectional view of an embodiment of an ultrasound catheter probe assembly 144. Items similar to those of the embodiment of FIG. 1 are designated by a prime symbol (') following the reference numeral. The catheter probe assembly 144 includes a catheter tip 101' attached to a catheter shaft 102'. Generally, the catheter probe assembly 144 includes a driveshaft 143 interconnected to the transducer array 107. The driveshaft 143 is operable to reciprocate and therefore reciprocate the transducer array 107 interconnected to it. An electrical interconnection member 111' includes a first portion 142 disposed in the distal end 103 of the catheter probe assembly 144 and operable to accommodate the reciprocal motion of the transducer array 107. The electrical interconnection member 111' further includes a second portion 113 disposed along the catheter shaft 102'. The electrical interconnection member 111' further includes a third portion 140 disposed along the catheter tip case 105' and operable to electrically interconnect the first portion 142 to the second portion 113.

The catheter probe assembly 144 may generally be sized and shaped for insertion into a patient and subsequent imaging of an internal portion of the patient. The catheter probe assembly 144 may generally include the distal end 103 and a proximal end (not shown). During imaging, the distal end 103 of the catheter probe assembly 144 may be disposed within the body of a patient. A catheter tip 101' may be disposed between the distal end 103 and a proximal end 104 of the catheter tip 101'. The catheter tip 101' may include a catheter tip case 105'. The catheter tip 101' may include a central axis 108. An enclosed volume 117' may be defined by the catheter tip case 105' and the driveshaft 143. The enclosed volume 117' may be fluid-filled and sealed.

The catheter shaft 102' may use any appropriate guidance method such as, but not limited to, a set of guide wires and associated controls. The catheter shaft 102' may be flexible and therefore be operable to be guided through and follow contours of the structure of the patient, such as the contours of the vasculature system.

The catheter probe assembly 144 includes the transducer array 107 and the array backing 128. Generally, the transducer array 107 is operable to transmit ultrasonic energy through the acoustic window 126 of the catheter tip case 105'. In general, the images generated by the catheter probe assembly 144 may be of a subject (e.g., internal structure of a patient) within an image volume 127'.

The transducer array 107 may be interconnected to the driveshaft 143, and the driveshaft 143 may be operable to reciprocally pivot the transducer array 107 about the central axis 108 such that the image plane is swept about the central axis 108 to form the image volume 127' as shown in FIG. 3. The sweeping of the image plane about the central axis 108 enables the transducer array 107 to scan the entire image volume 127' and thus a three dimensional image of the image volume 127' may be generated. The driveshaft 143 may be operable to reciprocally pivot the transducer array 107 at a rate sufficient enough to generate real-time or near real-time three-dimensional images of the image volume 127'. The transducer array 107 may be interconnected to the driveshaft at a proximal end of the transducer array 107.

The driveshaft 143, and therefore the transducer array 107 interconnected to the driveshaft 143, may be reciprocated using any appropriate means. For example, the proximal end of the catheter probe assembly 144 may include a motor capable of reciprocally driving the driveshaft 143 in both clockwise and counterclockwise directions. In this regard, the motor may be operable to reciprocally pivot the driveshaft 143 and therefore reciprocally pivot the transducer array 107 interconnected to the driveshaft 143.

When driveshaft 143 position is known, the corresponding position of the transducer array 107 will be known. Driveshaft 143 position may be tracked in any appropriate manner, such as through the use of an encoder and/or a magnetic position sensor.

The electrical interconnection member 111' may electrically interconnect the transducer array 107 with the ultrasound imaging apparatus. The electrical interconnection member 111' may be a multi-conductor cable comprising of a plurality of conductors arranged side-by-side with electrically nonconductive material between the conductors.

The electrical interconnection member 111' may be anchored such that a portion of it is fixed relative to the catheter tip case 105'. As noted above, the second portion 113 of the electrical interconnection member 111' may be secured to the catheter shaft 102'. Within the enclosed volume 117', the third portion 140 of the electrical interconnection member 111' may be secured to the inner surface of the catheter tip case 105'. The third portion 140 of the electrical interconnection member 111' may be secured to the catheter tip case 105' in a region corresponding to the position of the transducer array 107. In this regard, the third portion 140 of the electrical interconnection member 111' may be disposed such that it does not interfere with the reciprocal movement of the transducer array 107. Any appropriate method of anchoring the electrical interconnection member 111' to the catheter tip case 105' may be used. For example, adhesive may be used.

The first portion 142 of the electrical interconnection member 111' is operable to maintain an electrical connection to the transducer array 107 while the transducer array 107 is pivoting relative to the catheter tip case 105'. This may be achieved by coiling the first portion 142 of the electrical interconnection member 111' within the enclosed volume 117'. One end of the first portion 142 of the electrical interconnection member 111' may be anchored to the catheter tip case 105' at an anchor point 141 that is distal to the transducer array 107. The other end of the first portion 142 of the electrical interconnection member 111' may be electrically interconnected to the array backing 128 or to a flex board or other electrical member (not shown) that is in turn electrically interconnected to the transducer array 107. Where the electrical interconnection member 111' is ribbon shaped, the first portion 142 of the electrical interconnection member 111' may be disposed such that a top or bottom side of the ribbon faces and wraps about the central axis 108.

FIG. 3 illustrates a configuration where the first portion 142 of the electrical interconnection member 111' is helically disposed within the portion of the enclosed volume 117' distal to the transducer array 107. The first portion 142 of the electrical interconnection member 111' may be coiled about the central axis 108 a plurality of times. The first portion 142 of the electrical interconnection member 111' may be coiled about the central axis 108 such that the first portion 142 of the electrical interconnection member 111' forms a helix about the central axis 108. As in the embodiment of FIG. 1, by coiling the electrical interconnection member 111' about the central axis 108 a plurality of times, undesirable counteracting torque on the pivoting of the transducer array 107 may be significantly avoided.

In an embodiment, the first portion 142 of the electrical interconnection member 111' may include a total of about three revolutions about the central axis 108. The total length of the catheter tip case 105' may be selected to accommodate the number of revolutions needed for the first portion 142 of the electrical interconnection member 111'.

A distal end of the driveshaft 143 may be sealed along its outer perimeter using a sealing material 116'. The sealing material 116' may be disposed as illustrated between the driveshaft 143 and an inner surface of the catheter tip case 105'. In another embodiment, the outer layer 109' of the catheter shaft 102' may extend to or beyond the distal end of the driveshaft 143 and in such an embodiment, the sealing material 116' may be disposed between the driveshaft 143 and an inner surface of the outer layer 109'. The sealing material 116' may include any appropriate material and/or structure that allows relative rotational movement between the driveshaft 143 and the outer layer 109' while substantially preventing the flow of fluid from the enclosed volume 117' past the sealing material 116'. In another embodiment, the catheter shaft 102' may include an inner layer (similar to the inner layer 110 of FIG. 1) and the driveshaft 143 may be disposed within the inner layer. In such an embodiment, the inner layer, the outer layer 109', a volume between the inner layer and the outer layer 109', or any combination thereof, may house additional components, such as, for example, pull wires, reinforcing members and/or additional electrical conductors.

Figure 4A:
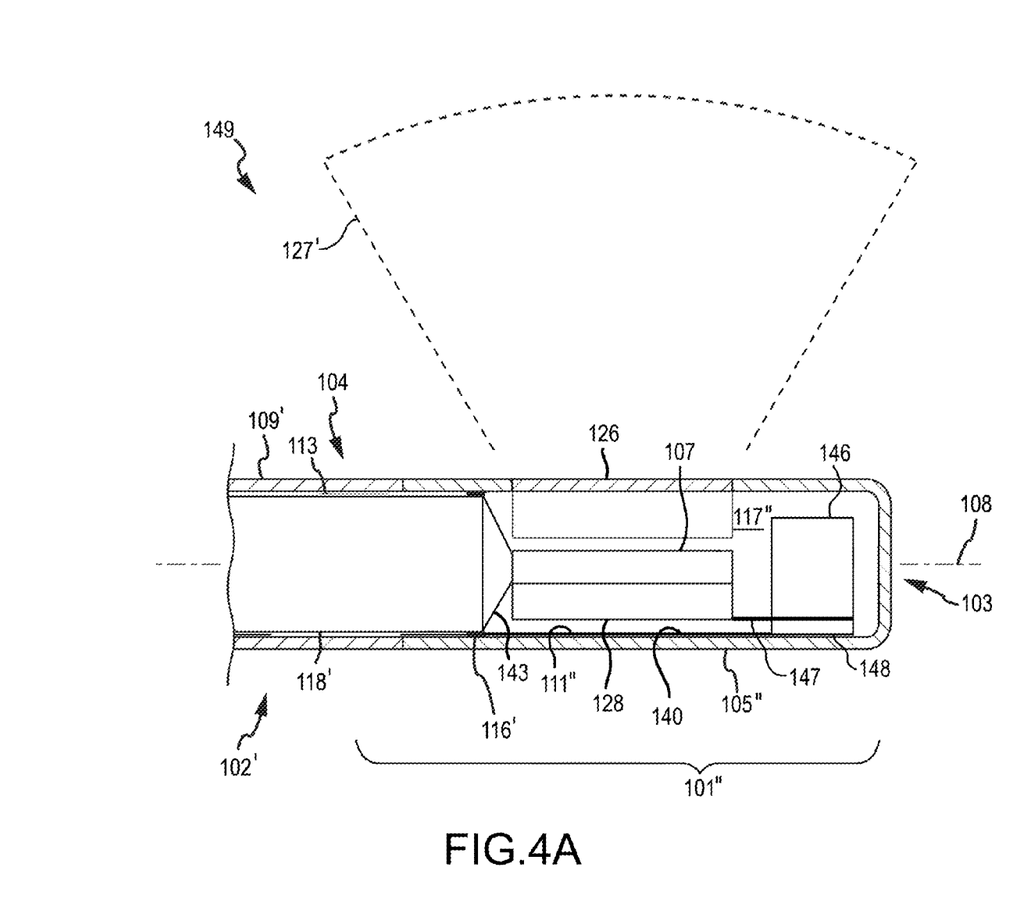
FIG. 4A is a partial cross-sectional view of an ultrasound catheter probe assembly.
Figure 4B:
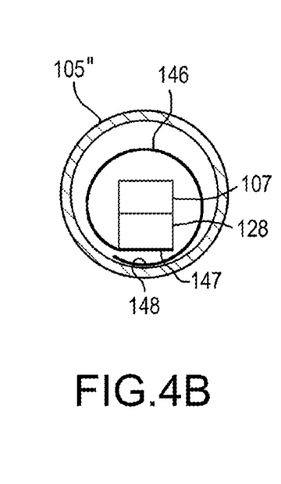
FIG. 4B is a partial cross-sectional end view of the ultrasound catheter probe assembly of FIG. 4A.

FIGS. 4A and 4B illustrate another embodiment of an ultrasound catheter probe assembly 149. Items similar to those of the embodiment of FIG. 3 are designated by a double prime symbol (") following the reference numeral. The catheter probe assembly 149 includes a catheter tip 101" attached to a catheter shaft 102'. Generally, the catheter probe assembly 149 includes a driveshaft 143 interconnected to the transducer array 107. An electrical interconnection member 111" includes a first portion 146 disposed in the distal end 103 of the catheter probe assembly 149 and operable to accommodate the reciprocal motion of the transducer array 107. The electrical interconnection member 111" further includes a second portion 113 disposed along the catheter shaft 102'. The electrical interconnection member 111" further includes a third portion 140 disposed along the catheter tip case 105"

and operable to electrically interconnect the first portion 146 to the second portion 113. An enclosed volume 117" may be defined by a catheter tip case 105" and the driveshaft 143. The enclosed volume 117" may be fluid-filled and sealed.

The catheter probe assembly 149 includes the transducer array 107 and the array backing 128. The transducer array 107 may be interconnected to the driveshaft 143, and the driveshaft 143 may be operable to reciprocally pivot the transducer array 107 about the central axis 108 such that the image plane is swept about the central axis 108 to form the image volume 127' as shown in FIG. 4A.

The electrical interconnection member 111" may electrically interconnect the transducer array 107 with the ultrasound imaging apparatus. The electrical interconnection member 111" may include a portion including a multi-conductor cable comprising of a plurality of conductors arranged side-by-side with electrically nonconductive material between the conductors. The electrical interconnection member 111" may further include a portion including flex board.

The electrical interconnection member 111" may be anchored such that a portion of it is fixed relative to the catheter tip case 105". As noted above, the second portion 113 of the electrical interconnection member 111" may be secured to the catheter shaft 102'. Within the enclosed volume 117", the third portion 140 of the electrical interconnection member 111" may be secured to the inner surface of the catheter tip case 105". The third portion 140 of the electrical interconnection member 111" may be secured to the catheter tip case 105" in a region corresponding to the position of the transducer array 107. In this regard, the third portion 140 of the electrical interconnection member 111" may be disposed such that it does not interfere with the reciprocal movement of the transducer array 107. Any appropriate method of anchoring the third portion 140 of the electrical interconnection member 111" to the catheter tip case 105" may be used. For example, adhesive may be used.

The first portion 146 of the electrical interconnection member 111" is operable to maintain an electrical connection to the transducer array 107 while the transducer array 107 is pivoting relative to the catheter tip case 105". This may be achieved by coiling the first portion 146 of the electrical interconnection member 111" within the enclosed volume 117". One end of the first portion 146 of the electrical interconnection member 111" may be anchored to the catheter tip case 105" at an anchor point 148 that is distal to the transducer array 107. The other end of the first portion 146 of the electrical interconnection member 111" may be electrically interconnected to a coil-to-backing portion 147 of the electrical interconnection member 111". The coil-to-backing portion 147 of the electrical interconnection member 111" may electrically interconnect the first portion 146 of the electrical interconnection member 111" to the array backing 128. The first portion 146 of the electrical interconnection member 111" may have a generally flat cross-section and be disposed such that a top or bottom side of the first portion 146 faces and wraps about the central axis 108. The first portion 146 of the electrical interconnection member 111" may be coiled in a "clock spring" arrangement where, as illustrated in FIGS. 4A and 4B, substantially the entirety of the first portion 146 of the electrical interconnection member 111" is positioned at the same point along the central axis 108. In this regard, a center line of the first portion 146 of the electrical interconnection member 111" may generally occupy a single plane that is disposed perpendicular to the central axis 108. One end of the clock spring of the first portion 146 of the electrical interconnection member 111" may be electrically interconnected to the third portion 140, while the other end may be electrically interconnected to the coil-to-backing portion 147. Although FIGS. 4A and 4B illustrates the clock spring of the first portion 146 as having a single coil, the clock spring of the first portion 146 may be comprised of more or less than a single coil. For example, in an embodiment, the clock spring of the first portion 146 may include 1.5 or 2 concentric coils (i.e., the clock spring of the first portion 146 may wrap around 1.5 or 2 times). In an arrangement, the clock spring of the first portion 146, the third portion 140, and the coil-to-backing portion 147 of the electrical interconnection member 111" may be constructed from a single flex board.

Similar to the embodiments of FIGS. 1 and 3, by coiling the clock spring of the first portion 146 the electrical interconnection member 111" (e.g., about an axis parallel to the central axis 108), undesirable counteracting torque on the pivoting of the transducer array 107 may be significantly avoided. In this regard, pivoting of the transducer array 107 about the central axis 108 in such a configuration may result in a slight tightening, or slight loosening, of the turns of the clock spring of the first portion 146 of the electrical interconnection member 111". Such a slight tightening and loosening may result in each coil (e.g., each individual rotation of the clock spring about the central axis 108) producing only a small lateral displacement and corresponding displacement of fluid.

In alternate configurations of the catheter probe assemblies 144, 149 of FIGS. 3 and 4A, motors (not shown) may be used in place of the driveshafts 143. Such motors may be located near the proximal ends of the catheter tips 101', 101". Such motors may be disposed within the enclosed volumes 117', 117", or they may be disposed outside of the enclosed volumes 117', 117".

Similar to as described above with reference to FIG. 1, in alternate embodiments, the catheter tip cases 105', 105" of the embodiments of FIGS. 3 and 4A may be in the form of a protective cages disposed about the electrical interconnection members 111', 111", arrays 107, and other appropriate components of the catheter probe assemblies 144, 149. Such cages may allow blood (or other bodily fluid) into the volumes corresponding to the enclosed volumes 117', 117", of the embodiments of FIGS. 3 and 4A. The cages may be open enough to allow blood to flow throughout the volumes corresponding to the enclosed volumes 117', 117", yet have enough structure to assist in protecting blood vessels and/or other patient structures from damage from contact with the catheter probe assemblies 144, 149. Moreover, and similar to as discussed above, rounded acoustic structures may be interconnected to the arrays 107. Other components may also be shaped to help reduce turbulence, avoid thrombogenicity, and avoid damage to blood cells.

In both embodiments that include an enclosed volume within a catheter tip case, and embodiments where the catheter tip case is a cage that is open to the surrounding environment, the portion of the catheter tip case in the region of the first portion of the electrical interconnect 112 may be steerable and/or flexible. In such a steerable and/or flexible configuration, the mechanical stresses due to steering and/or flexing on the first portion of the electrical interconnect 112 may be distributed over substantially the entire first portion 112.

Additional modifications and extensions to the embodiments described above will be apparent to those skilled in the art. Such modifications and extensions are intended to be within the scope of the present invention as defined by the claims that follow.

What is claimed is:

1. An ultrasound catheter probe comprising:
   a catheter having a flexible catheter shaft and a catheter tip case, the catheter tip case having an enclosed volume distal to the catheter shaft;
   an ultrasound transducer array disposed for reciprocal pivotal movement about a pivot axis within said enclosed volume, the ultrasound transducer array comprising a plurality of ultrasonic transducers disposed along the pivot axis; and
   at least a first electrical interconnection member comprising a plurality of conductors arranged side-by-side with electrically non-conductive material therebetween, and having a first portion and a second portion, the first portion coiled within said enclosed volume and electrically interconnected to said ultrasound transducer array, and the second portion helically and fixedly positioned disposed in and along the flexible catheter shaft, wherein upon said reciprocal pivotal movement said coiled first portion of said first electrical interconnection member tightens and loosens.

2. An ultrasound catheter probe as recited in claim 1, wherein said first portion of said first electrical interconnection member is helically disposed within said enclosed volume about a helix axis.

3. An ultrasound catheter probe as recited in claim 2, wherein upon said reciprocal pivotal movement said helically wrapped first portion of said first electrical interconnection member tightens and loosens about said helix axis.

4. An ultrasound catheter probe as recited in claim 3, wherein said pivot axis is coincident with said helix axis.

5. An ultrasound catheter probe as recited in claim 1, said a second portion adjoining said first portion and being disposed between an outer layer and inner layer of the catheter shaft.

6. An ultrasound catheter probe as recited in claim 1, said a second portion adjoining said first portion and being wrapped about and bonded to an inner core member disposed within an outer layer of said catheter shaft.

7. An ultrasound catheter probe as recited in claim 1, wherein said first electrical interconnection member is ribbon-shaped.

8. An ultrasound catheter probe as recited in claim 7, wherein said first portion of said first electrical interconnection member is helically disposed within said enclosed volume about a helix axis.

9. An ultrasound catheter probe as recited in claim 8, wherein upon said reciprocal pivotal movement said helically wrapped first portion of said first electrical interconnection member tightens and loosens about said helix axis.

10. An ultrasound catheter probe as recited in claim 8, further comprising a motor operable to produce said reciprocal pivotal movement, wherein a flex board is electrically interconnected to said ultrasound transducer array, wherein said first electrical interconnection member is electrically interconnected to said flex board at a first electrical interconnection member to flex board connection, wherein said first electrical interconnection member to flex board connection is disposed between said motor and an outer wall of said catheter.

11. An ultrasound catheter probe as recited in claim 10, further comprising a cylindrical interconnection support, wherein said first electrical interconnection member to flex board connection is attached to said cylindrical interconnection support.

12. An ultrasound catheter probe as recited in claim 1, wherein said first portion of said first electrical interconnection member is coiled a plurality of times within said enclosed volume.

13. An ultrasound catheter probe as recited in claim 1, wherein said first portion of said first electrical interconnection member is helically disposed about said pivot axis a plurality of times.

14. An ultrasound catheter probe as recited in claim 1, wherein said catheter tip case having said enclosed volume is located at a distal end of said ultrasound catheter probe.

15. An ultrasound catheter probe as recited in claim 1, wherein said ultrasound catheter probe has a round cross-sectional profile.

16. An ultrasound catheter probe as recited in claim 1, further comprising a sealable port.

17. An ultrasound catheter probe as recited in claim 1, further comprising a motor disposed within said enclosed volume and operatively interconnected to said ultrasound transducer array, wherein said motor drives said array for said reciprocal pivotal movement.

18. An ultrasound catheter probe as recited in claim 1, further comprising a driveshaft operatively interconnected to said ultrasound transducer array, wherein said driveshaft drives said array for said reciprocal pivotal movement.

19. An ultrasound catheter probe as recited in claim 18, wherein said ultrasound catheter probe comprises a distal end and a proximal end, wherein said driveshaft extends from said proximal end to said ultrasound transducer array.

20. An ultrasound catheter probe as recited in claim 1, wherein said ultrasound catheter probe comprises a distal end and a proximal end, wherein said first portion is disposed closer to said distal end than said ultrasound transducer array, and wherein said first portion is helically disposed within said enclosed volume about a helix axis.

21. An ultrasound catheter probe as recited in claim 1, wherein said first portion of said first electrical interconnection member is disposed in a clock spring arrangement.

22. An ultrasound catheter probe as recited in claim 21, wherein a center line of said first portion of said first electrical interconnection member is disposed within a single plane that is disposed perpendicular to said pivot axis.

23. An ultrasound catheter probe as recited in claim 22, wherein said ultrasound catheter probe comprises a distal end and a proximal end, wherein said first portion of the first electrical interconnection member is disposed closer to said distal end than said ultrasound transducer array.

24. An ultrasound catheter probe as recited in claim 23, wherein said pivot axis coincides with a central axis of said catheter tip case, wherein said first portion comprises a flex board.

25. An ultrasound catheter probe as recited in claim 1, further comprising a lumen, wherein a portion of said lumen is disposed within a coil of said first portion of said first electrical interconnection member.

26. An ultrasound catheter probe as recited in claim 25, wherein said ultrasound catheter probe comprises a distal end and a proximal end, wherein said lumen extends from said coil of said first portion of said first electrical interconnection member to said proximal end.

27. An ultrasound catheter probe as recited in claim 1, further comprising a fluid disposed within said enclosed volume.

28. An ultrasound catheter probe as recited in claim 1, further comprising at least a first insulator layer on said first portion of said first electrical interconnection member within said enclosed volume.

* * * * *